US008153018B2

(12) United States Patent
Johnson et al.

(10) Patent No.: US 8,153,018 B2
(45) Date of Patent: Apr. 10, 2012

(54) METHODS FOR MAKING 3-CHLORO-1,1,1,6,6,6-HEXAFLUORO-2,4-HEXADIENE

(75) Inventors: Robert C. Johnson, Lancaster, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/249,380

(22) Filed: Sep. 30, 2011

(65) Prior Publication Data

US 2012/0022300 A1    Jan. 26, 2012

Related U.S. Application Data

(63) Continuation of application No. 12/722,632, filed on Mar. 12, 2010, now Pat. No. 8,044,015.

(51) Int. Cl.
*C09K 5/04* (2006.01)

(52) U.S. Cl. ............... 252/67; 510/412; 570/164

(58) Field of Classification Search ............ 252/67; 510/412; 570/164
See application file for complete search history.

(56) References Cited

U.S. PATENT DOCUMENTS

| | | | |
|---|---|---|---|
| 2,834,748 A | 5/1958 | Bailey et al. | |
| 2,846,458 A | 8/1958 | Haluska | |
| 2,917,480 A | 12/1959 | Bailey et al. | |
| 3,085,918 A | 4/1963 | Sherliker et al. | |
| 6,023,004 A * | 2/2000 | Thenappan et al. | 570/188 |
| 6,030,934 A * | 2/2000 | Owens et al. | 510/411 |
| 6,281,185 B1 * | 8/2001 | Owens et al. | 510/411 |
| 6,516,837 B2 | 2/2003 | Thomas et al. | |
| 6,689,924 B1 * | 2/2004 | Thenappan et al. | 570/167 |
| 7,214,839 B2 * | 5/2007 | Tung et al. | 570/163 |
| 8,044,015 B2 * | 10/2011 | Johnson et al. | 510/408 |
| 2010/0016457 A1 * | 1/2010 | Bowman et al. | 521/82 |
| 2011/0224125 A1 * | 9/2011 | Johnson et al. | 510/412 |
| 2011/0245549 A1 * | 10/2011 | Merkel et al. | 570/157 |
| 2012/0022300 A1 * | 1/2012 | Johnson et al. | 570/153 |

OTHER PUBLICATIONS

Lu, et al., Anesthesia. XLI: The Anesthetic Properties of Certain Fluorinated Hydrocarbons and Ethers, Anesthesiology, vol. 14, pp. 466-472, 1953.

* cited by examiner

*Primary Examiner* — Gregory Webb
(74) *Attorney, Agent, or Firm* — Bruce O. Bradford

(57) ABSTRACT

Disclosed are compositions and systems having utility in numerous situations, including in particular solvent cleaning systems, as well as refrigerant lubricants and/or compatibilizing agents, and to methods which utilize such compositions and systems. More particularly, the present invention in preferred aspects is directed to solvents, blowing agents, heat transfer fluids and compatibilizing agents comprising the compound 3-chloro-1,1,1,6,6,6-hexafluoro-2,4-hexadiene. In particular, this invention provides a method for the production of the compound of Formula I, 3-chloro-1,1,1,6,6,6-hexafluoro-2,4-hexadiene, comprising reacting 1,1,1,3,3-pentachloropropane with hydrogen fluoride in the presence of a catalyst, in a reactor.

12 Claims, No Drawings

METHODS FOR MAKING 3-CHLORO-1,1,1,6,6,6-HEXAFLUORO-2,4-HEXADIENE

CROSS-REFERENCE TO RELATED APPLICATION

This application is a continuation of patent application Ser. No. 12/722,632, filed Mar. 12, 2010, now U.S. Pat. No. 8,044,015, the disclosure of which is hereby incorporated herein by reference.

BACKGROUND OF THE INVENTION

Solvent compositions are in widespread use throughout the world and in a wide variety of industrial applications. Certain fluorocarbons have been preferred components in solvent cleaning systems for many years. Trichlorotrifluoroethane has been one of the most widely used fluorocarbon solvents in recent years because it is generally effective as a solvent for many greases, oils, waxes and the like, and has therefore found widespread use for cleaning electric motors, compressors, heavy metal parts, delicate precision metal parts, printed circuit boards, gyroscopes, guidance systems, aerospace and missile hardware, aluminum parts, and the like. Furthermore, trichlorotrifluoroethane is advantageous because it is non-toxic and nonflammable. Trichlorotrifluoroethane has two isomers: 1,1,2-trichloro-1,2,2-trifluoroethane (known in the art as CFC-113) and 1,1,1-trichloro-2,2,2-trifluoroethane (known in the art as CFC-113a).

Concern has increased in recent years about potential damage to the earth's ozone layer, and certain chlorine-based compounds have been identified as particularly problematic in this regard. CFC-113 is chemically stable and therefore has a relatively long life in the stratosphere, and since the use CFC-113 as a solvent will frequently result in its release into the environment, it will frequently reach the stratosphere. In the stratosphere, CFC-113 gives rise to photolysis under the influence of sun light to generate chlorine radicals. The thus generated chlorine radicals combine with ozone, resulting in ozone depletion. Accordingly, the use of organic chlorine-based compounds such as CFCs has been severely restricted in many countries of the world by governmental regulation. Because CFC-113 has a high ozone depletion potential (ODP), a need has risen to replace it, and other compounds which exhibit similar environmentally detrimental properties.

Applicants have thus come to appreciate a continuing need for low ODP and low global warming potential (GWP) solvent compositions that are potentially useful in numerous applications, including degreasing applications, precision cleaning and electronics cleaning applications, dry cleaning applications, solvent etching applications, as a solvent in aerosols or other sprayable compositions, as carrier solvents for depositing lubricants and release agents and other solvent or surface treatment applications.

In many applications it is also highly desirable for solvent compositions to be relatively stable, that is, to be relatively resistant to possible chemical changes during storage and use. Applicants have come to recognize that CFC-113 is deficient in this regard because it tends to hydrolyze and form HCl. Furthermore, this problem is worsened because metal, which is typically present during any solvent cleaning operations, acts as a catalyst and causes the hydrolysis of CFC-113 to increase dramatically.

The compositions of the present invention are thus part of a continued search for the next generation of low global warming potential materials. Such materials must have low environmental impact, as measured by ultra-low global warming potential and zero ozone depletion potential.

The preferred compositions of the present invention are environmentally acceptable and do not to contribute to the depletion of the earth's stratospheric ozone layer. The compounds and compositions of the present invention have no substantial ozone depletion potential, preferably an ODP of not greater than about 0.5 and even more preferably an ODP of not greater than about 0.25, most preferably an ODP of not greater than about 0.1; a global warming potential (GWP) of not greater than about 150, and even more preferably, a GWP of not greater than about 50.

As used herein, ODP is defined in the "Scientific Assessment of Ozone Depletion, 2002, " a report of the World Meteorological association, incorporated here by reference.

As used herein, GWP is defined relative to that of carbon dioxide and over a 100 year time horizon, and defined in the same reference as for the ODP mentioned above.

As used herein, the term "nonflammable" refers to compounds or compositions which do not exhibit a flashpoint as measured by one of the standard flash point methods, for example ASTM-1310-86 "Flash point of liquids by tag Open-cup apparatus." Unfortunately, many HFC's which might otherwise be desirable for use in solvent compositions are flammable. For example, the fluoroalkane pentafluorobutane (HFC-365) is flammable and therefore not viable for use in many applications.

SUMMARY OF THE INVENTION

This invention relates to compositions and systems having utility in numerous situations, including particular solvent cleaning systems, as well as refrigerant lubricants and/or compatibilizing agents, and to methods which utilize such compositions and systems. More particularly, the present invention in preferred aspects is directed to solvents, blowing agents, heat transfer fluids and compatibilizing agents comprising the compound 3-chloro-1,1,1,6,6,6-hexafluoro-2,4-hexadiene (hereinafter, Formula I, which includes all isomers thereof).

In particular, this invention provides a method for the production of the compound of Formula I, 3-chloro-1,1,1,6,6,6-hexafluoro-2,4-hexadiene, comprising reacting 1,1,1,3,3-pentachloropropane with hydrogen fluoride in the presence of a catalyst, in a reactor.

In certain embodiments, the hydrogen fluoride is anhydrous HF. In certain embodiments, the catalyst is a liquid phase catalyst. In certain embodiments, the liquid phase catalyst comprises titanium tetrachloride. In certain embodiments, the catalyst comprises fluorinated titanium tetrachloride. In certain embodiments, the reaction is conducted at a temperature in the range of from 80° C. to 100° C. In certain embodiments, the reaction is conducted at a pressure of from 100 psig to 110 psig.

In certain embodiments, another compound, 1-chloro-3,3,3-trifluoropropene (1233zd(E)), is formed during the reaction. In certain embodiments, the compound 1-chloro-3,3,3-trifluoropropene (1233zd(E)) is separated from the compound of Formula I, 3-chloro-1,1,1,6,6,6-hexafluoro-2,4-hexadiene. In certain embodiments, these compounds are separated by the use of a distillation column attached to the reactor. In certain embodiments, the compound 1-chloro-3,3,3-trifluoropropene (1233zd(E)) is removed from the top of the distillation column. In certain embodiments, the compound of Formula I, 3-chloro-1,1,1,6,6,6-hexafluoro-2,4-hexadiene, is removed from the bottom of the distillation column.

DETAILED DESCRIPTION OF PREFERRED EMBODIMENTS

The compound of Formula I displays characteristics which will make it an excellent solvent, such as:

(a) because the compound contains one chlorine molecule, the compound's ability to dissolve organic materials will be substantial;
(b) because of the presence of terminal trifluoromethyl groups, the compound will have low surface tension (important for organic solvents) and good compatibility with fluorinated materials, which are generally difficult to dissolve;
(c) based on the compound's elution time in gas chromatography, it should have very good volatility for solvent applications (similar to perchloroethene);
(d) because the compound contains double bonds, the compound's atmospheric lifetime and therefore Global Warming Potential and Ozone Depletion Potential will be quite low; and
(e) finally, because this material can be made from inexpensive raw materials, so that it can be priced attractively compared to other comparable solvent materials.

Applicants have found that the above-noted and other needs can be satisfied, and many of the above-noted deficiencies and others can be overcome, by compositions comprising a compound of Formula I.

Applicants have also discovered methods and systems for removing contaminants from a product, part, component, substrate, or any other article or portion thereof by applying to the article a composition containing a compound of Formula I.

For the purposes of convenience, the term "article" is used herein to refer to all such products, parts, components, substrates, and the like and is further intended to refer to any surface or portion thereof. Furthermore, the term "contaminant" is intended to refer to any unwanted material or substance present on the article, even if such substance is placed on the article intentionally. For example, in the manufacture of semiconductor devices it is common to deposit a photoresist material onto a substrate to form a mask for the etching operation and to subsequently remove the photoresist material from the substrate. The term "contaminant" as used herein is intended to cover and encompass such a photo resist material.

A. Compositions

This invention relates to compositions and systems having utility in numerous situations, including particular solvent cleaning systems, as well as refrigerant lubricants and/or compatibilizing agents, and to methods which utilize such compositions and systems.

More particularly, the present invention in preferred aspects is directed to solvents, blowing agents, heat transfer fluids and compatibilizing agents comprising the compound of Formula I, namely 3-chloro-1,1,1,6,6,6-hexafluoro-2,4-hexadiene, including all isomers thereof.

It is contemplated that all compositions containing the compound of Formula I as identified above are adaptable for use in certain aspects of the present invention. The preferred compositions and methods of the present invention preferably exhibit one or more, and preferably all, of the following properties: chemical stability; no substantial ozone depleting potential (ODP); relatively high degree of miscibility with common contaminants, particularly mineral oil and/or silicone oil; low or no flammability; low or no toxicity; and low or no global warming potential (GWP).

While the actual GWP has not been measured, based on its structure, it will likely be below 20 (where the GWP of $CO_2$ is 1). Similarly, the actual boiling point of the compound has not been precisely determined. However, based on the structure, it should be approximately 82° C. This boiling point is in the range of similar solvents such as 1,1,1-trichloroethane (75° C.), trichloroethylene (87° C.). The 82° C. boiling point is also consistent with the characteristics of the compound as seen in the operating unit during the manufacture of the compound.

Also, the preferred compositions containing the compound of Formula I are miscible with greater than 20% by weight of mineral oil and/or silicone oil, more preferably in a weight ratio in the range of at least about 80:20 to about 20:80, and even more preferably in substantially all proportions.

As used herein, miscibility is measured in accordance with visual evaluation of phase formation or separation when two liquids are mixed together, as is known to those skilled in the art.

The compositions of the present invention thus generally possess properties and characteristics that are highly desirable for use in connection with many different applications, including many different types of cleaning and contaminant removal applications.

B. Cleaning Compositions

One of the most important characteristic of the present invention as it relates to cleaning applications is that the present compositions have been found to have a high level of solvent power for many common contaminants and residues while at the same time not having a high degree of acute toxicity, as measured by exposure to mice and rats. Toxicity testing is conducted in accordance with the methods published in Anesthesiology, Vol. 14, pp. 466-472, 1953.

In certain preferred embodiments, the solvent cleaning composition comprises a compound of Formula I having an acute toxicity level substantially less than, and preferably at least about 30 relative percent less than, the toxicity level of HFO-1223xd.

One aspect of the present intervention thus provides surface treatment compositions comprising at least a substantial amount of the compound of Formula I having an acute toxicity level substantially less than, and preferably at least about 30 relative percent less than, the toxicity level of HFO-1223xd.

However, it is also contemplated that in many embodiments the composition will include other components in addition to the above-noted compound of Formula I. For example, it is contemplated that in certain embodiments the surface treating compositions may include co-solvents, anticorrosive agents, surfactants, stabilizers, inhibitors and other adjuvants which assist with or enhance the functionality of the composition. Examples of co-solvents include linear, branched and cyclic hydrocarbons, halocarbons, including chlorinated and brominated compounds, alcohols, such as methanol, ethanol, propanol, isopropanol, butanol, etc., ketones, esters, ethers and acetals. Examples of stabilizers include nitroalkanes, epoxy alkanes and phosphite esters. Some of these form azeotrope-like compositions with HFO-1214, HFO-1233, and/or HFO-1354.

It is likely that azeotrope-like compositions are formed, but these have not been measured. Use of additives to tailor the properties of solvents is common, and it is likely that the performance of other solvents could be enhanced by addition of small quantities of the subject compound.

Although it is contemplated that the compositions of the present invention may include the compounds of the present invention in widely ranging amounts, it is generally preferred that the solvent cleaning compositions of the present invention comprise a compound in accordance with Formula I in an amount that is at least about 25% by weight, preferably at least about 50% by weight, more preferably at least about 75% by weight and most preferably at least about 90% by weight, of the composition.

In certain embodiments the present compositions are well adapted for used in the form of an aerosol and/or a sprayable composition, and in such embodiments it is contemplated that the present compositions may have one or more additives designed for this use, such as propellants, atomizing agents and the like.

C. Heat Transfer Compositions

It is contemplated that when the compositions of the present invention are used in heat transfer applications, such compositions may include the compounds of the present invention in widely ranging amounts. It is generally preferred, however, that the heat transfer compositions of the present invention, especially the refrigerant compositions of the present invention, comprise the compound of Formula I having an acute toxicity level substantially less than, and preferably at least about 30 relative percent less than, the toxicity level of HFO-1223xd, in an amount that is at least about 50% by weight, and even more preferably at least about 70% by weight, of the composition.

The heat transfer compositions of the present invention may include other components for the purpose of enhancing or providing certain functionality to the composition, or in some cases to reduce the cost of the composition. For example, refrigerant compositions according to the present invention, especially those used in vapor compression systems, include a lubricant, generally in amounts of from about 30 to about 50 percent by weight of the composition.

Furthermore, the present compositions may also include a compatibilizer, such as propane, for the purpose of aiding compatibility and/or solubility of the lubricant. Such compatibilizers, including propane, butanes and pentanes, are preferably present in amounts of from about 0.5 to about 5 percent by weight of the composition.

Combinations of surfactants and solubilizing agents may also be added to the present compositions to aid oil solubility, as disclosed by U.S. Pat. No. 6,516,837, the disclosure of which is hereby incorporated by reference. Commonly used refrigeration lubricants such as Polyol Esters (POEs) and Poly Alkylene Glycols (PAGs) that are used in refrigeration machinery with hydrofluorocarbon (HFC) refrigerants may be used with the refrigerant compositions of the present invention.

For compatibilizing compositions of the present invention, it may be preferred to include in such compositions co-solvents, anticorrosive agents, surfactants, stabilizers and other adjuvants which assist with or enhance the functionality of the composition. For preferred compatibilizing compositions of the present invention, the compound of Formula I, preferably having an acute toxicity level substantially less than, and preferably at least about 30 relative percent less than, the toxicity level of HFO-1223xd, are present in an amount that is at least about 25% by weight, and even more preferably at least about 50% by weight, of the composition.

D. Blowing Agents, Foams and Foamable Compositions

Blowing agents may also comprise or constitute the compound of Formula I or a composition comprising the compound. As mentioned above, the compositions of the present invention may include the compound of Formula I in widely ranging amounts. It is generally preferred, however, that for preferred compositions for use as blowing agents in accordance with the present invention, the compound of Formula I is present in an amount that is at least about 5% by weight, and even more preferably at least about 15% by weight, of the composition.

In other embodiments, the invention provides foamable compositions, and preferably polyurethane, polyisocyanurate and extruded thermoplastic foam compositions, prepared using the compound of Formula I or compositions comprising the compound. In such foam embodiments, one or more of the compositions may be included as or part of a blowing agent in a foamable composition, which composition preferably includes one or more additional components capable of reacting and/or foaming under the proper conditions to form a foam or cellular structure, as is well known in the art. The invention also relates to foam, and preferably closed cell foam, prepared from a polymer foam formulation containing a blowing agent comprising the compositions of the invention. In yet other embodiments, the invention provides a foamable composition comprising thermoplastic foams, such as polystyrene and polyethylene (PE), preferably low density PE.

In certain preferred embodiments, dispersing agents, cell stabilizers, surfactants and other additives may also be incorporated into the blowing agent compositions of the present invention. Surfactants are optionally but preferably added to serve as cell stabilizers. Some representative materials are sold under the names of DC-193, B-8404, and L-5340 which are, generally, polysiloxane polyoxyalkylene block co-polymers such as those disclosed in U.S. Pat. Nos. 2,834,748, 2,917,480, and 2,846,458, each of which is hereby incorporated herein by reference.

Other optional additives for the blowing agent mixture may include flame retardants such as tri-(2-chloroethyl)-phosphate, tri-(2-chloropropyl)-phosphate, tri-(2,3-dibromopropyl)-phosphate, tri-(1,3-dichloropropyl)-phosphate, diammonium phosphate, various halogenated aromatic compounds, antimony oxide, aluminum trihydrate, polyvinyl chloride, and the like.

E. Methods and Systems

The compound of Formula I and compositions comprising the compound are also useful in connection with numerous methods and systems, including; as a solvent in solvent cleaning methods, particularly vapor degreasing; heat transfer fluids in methods and systems for transferring heat, such as refrigerants used in refrigeration, air conditioning and heat pump systems; as a component in methods and systems for extinguishing and suppressing fire; as an additive to reduce the flammability of fluids; and as a component involved in the formation of foam, foam premixes, foam products and blowing agents for foams.

F. Cleaning Methods

The contaminant removal aspects of the present invention comprise contacting the contaminated article with the compound of Formula I or a composition including the compound of Formula I. In preferred embodiments, the methods comprise applying a solvent composition of the present invention to the article containing the contaminant, with vapor degreasing and solvent cleaning methods being particularly preferred for certain applications, especially those especially intricate parts and difficult to remove soils. As those skilled in the art will appreciate, the present methods have applicability to a wide variety of different cleaning and residue removal techniques, and all such techniques are within the broad scope of the present invention.

Preferred cleaning methods of the present invention comprise applying the present composition to the article, with vapor degreasing and solvent cleaning methods being particularly preferred for certain applications, especially those involving intricate parts and difficult to remove soils. Preferred vapor degreasing and solvent cleaning methods consist of exposing an article, preferably at room-temperature, to the vapors of a boiling solvent. Vapors condensing on the object have the advantage of providing a relatively clean, distilled solvent to wash away grease or other contamination. Such processes thus have an additional advantage in that final evaporation of the present solvent composition from the object leaves behind relatively little residue as compared to the case where the object is simply washed in liquid solvent.

For applications in which the article includes contaminants that are difficult to remove, it is preferred that the present methods involve raising the temperature of the solvent composition of the present invention above ambient or to any other temperature that is effective in such application to substantially improve the cleaning action of the solvent. Such processes are also generally preferred for large volume assembly line operations where the cleaning of article, particularly metal parts and assemblies, must be done efficiently and quickly.

In preferred embodiments, the cleaning methods of the present invention comprise immersing the article to be cleaned in liquid solvent at an elevated temperature, and even more preferably at about the boiling point of the solvent. In such operations, this step preferably removes a substantial amount, and even more preferably a major portion, of the target contaminant from the article. This step is then preferably followed by immersing the article in solvent, preferably freshly distilled solvent, which is at a temperature below the temperature of the liquid solvent in the preceding immersion step, preferably at about ambient or room temperature. The preferred methods also include the step of then contacting the article with relatively hot vapor of the present solvent composition, preferably by exposing the article to solvent vapors rising from the hot/boiling solvent associated with the first mentioned immersion step. This preferably results in condensation of the solvent vapor on the article. In certain preferred embodiments, the article may be sprayed with distilled solvent before final rinsing.

It is contemplated that numerous varieties and types of vapor degreasing equipment are adaptable for use in connection with the present methods. One example of such equipment and its operation is disclosed in U.S. Pat. No. 3,085,918, which is hereby incorporated herein by reference. The equipment disclosed therein includes a boiling sump for containing a solvent composition, a clean sump for containing distilled solvent, a water separator, and other ancillary equipment.

The present cleaning methods may also comprise cold cleaning in which the contaminated article is either immersed in the fluid composition of the present invention under ambient or room temperature conditions or wiped under such conditions with rags or similar objects soaked in solvents. In addition, the present methods may comprise or consist essentially of applying the present composition to the article by spraying the composition onto the article.

G. Heat Transfer Methods

The preferred heat transfer methods generally comprise providing the compound of Formula I or a composition comprising the compound of Formula I and causing heat to be transferred to or from the composition changing the phase of the composition. For example, the present methods provide cooling by absorbing heat from a fluid or article, preferably by evaporating the present refrigerant composition in the vicinity of the body or fluid to be cooled to produce vapor comprising the present composition. Preferably the methods include the further step of compressing the refrigerant vapor, usually with a compressor or similar equipment to produce vapor of the present composition at a relatively elevated pressure.

Generally, the step of compressing the vapor results in the addition of heat to the vapor, thus causing an increase in the temperature of the relatively high pressure vapor. Preferably, the present methods include removing from this relatively high temperature, high pressure vapor at least a portion of the heat added by the evaporation and compression steps. The heat removal step preferably includes condensing the high temperature, high pressure vapor while the vapor is in a relatively high pressure condition to produce a relatively high pressure liquid comprising a composition of the present invention. This relatively high pressure liquid preferably then undergoes a nominally isoenthalpic reduction in pressure to produce a relatively low temperature, low pressure liquid. In such embodiments, it is this reduced temperature refrigerant liquid which is then vaporized by heat transferred from the body or fluid to be cooled.

In another process embodiment of the invention, the compound of Formula I and compositions comprising the compound may be used in a method for producing heating which comprises condensing a refrigerant comprising the compositions in the vicinity of a liquid or body to be heated. Such methods, as mentioned hereinbefore, frequently are reverse cycles to the refrigeration cycle described above.

The present invention also includes the use of the compound of Formula I and compositions comprising the compound in connection with heat transfer methods comprising adding and/or removing sensible heat from the compound or compositions, preferably by bringing the compound or compositions into convective or conductive heat transfer relationship with an article or fluid to be heated or cooled. Such contact is most preferably indirect contact, such as would occur through the present composition being exposed to a heat transfer surface located on one side of a fluid transfer barrier. Typically, the article or fluid to be cooled or heated is located on the other side of such a barrier but in contact with a surface that is thermodynamically coupled to the heat transfer surface in contact with the compound of Formula I or compositions comprising the compound. Finned tube heat exchangers are common example of such an apparatus, which also may be used in connection with phase change heat transfer as discussed above.

H. Flammability Reduction Methods

According to certain other preferred embodiments, the present invention provides methods for reducing the flammability of fluids, the methods comprising adding the compound of Formula I or a composition comprising the compound to the fluid. The flammability associated with any of a wide range of otherwise flammable fluids may be reduced according to the present invention. For example, the flammability associated with fluids such as ethylene oxide, flammable hydrofluorocarbons and hydrocarbons, including: HFC-365, hexane, octane, and the like can be reduced according to the present invention. For the purposes of the present invention, a flammable fluid may be any fluid exhibiting flammability ranges in air as measured via any standard conventional test method, such as ASTM E-681, and the like.

Any suitable amounts of the compound of Formula I or compositions comprising the compound may be added to reduce flammability of a fluid according to the present invention. As will be recognized by those of skill in the art, the amount added will depend, at least in part, on the degree to which the subject fluid is flammable and the degree to which it is desired to reduce the flammability thereof. In certain preferred embodiments, the amount of compound or composition added to the flammable fluid is effective to render the resulting fluid substantially non-flammable.

I. Flame Suppression Methods

The present invention further provides methods of suppressing a flame, the methods comprising contacting a flame with a fluid comprising the compound of Formula I or a composition comprising the compound. Any suitable methods for contacting the flame with the compound of Formula I or a composition comprising the compound may be used. For example, a composition comprising the compound of Formula I may be sprayed, poured, and the like onto the flame, or at least a portion of the flame may be immersed in the composition. In light of the teachings herein, those of skill in the art will be readily able to adapt a variety of conventional apparatus and methods of flame suppression for use in the present invention.

J. Foam Blowing Methods

One embodiment of the present invention relates to methods of forming foams, and preferably polyurethane and polyisocyanurate foams. The methods generally comprise providing a blowing agent composition comprising the compound of Formula I or a composition comprising the compound, adding (directly or indirectly) the blowing agent composition to a foamable composition, and reacting the foamable composition under the conditions effective to form a foam or cellular structure, as is well known in the art. Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention. In general, such preferred methods comprise preparing polyurethane or polyisocyanurate foams by combining an isocyanate, a polyol or mixture of polyols, a blowing agent or mixture of blowing agents comprising one or more of the present compositions, and other materials such as catalysts, surfactants, and optionally, flame retardants, colorants, or other additives.

It is convenient in many applications to provide the components for polyurethane or polyisocyanurate foams in pre-blended formulations. Most typically, the foam formulation is pre-blended into two components. The isocyanate and optionally certain surfactants and blowing agents comprise the first component, commonly referred to as the "A" component. The polyol or polyol mixture, surfactant, catalysts, blowing agents, flame retardant, and other isocyanate reactive components comprise the second component, commonly referred to as the "B" component. Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, and even other polyols can be added as a third stream to the mix head or reaction site. Most preferably, however, they are all incorporated into one B-component as described above.

It is also possible to produce thermoplastic foams using the compound of Formula I or a composition comprising the compound. For example, conventional polystyrene and polyethylene formulations may be combined with the compositions in a conventional manner to produce rigid foams.

K. Synthesis of the Compound of Formula I:

The compound of Formula I, namely 3-chloro-1,1,1,6,6,6-hexafluoro-2,4-hexadiene, is formed by reacting 1,1,1,3,3-pentachloropropane with anhydrous hydrogen fluoride in the presence of liquid-phase titanium tetrachloride-based catalyst.

The compound of Formula I was formed when 1,1,1,3,3-pentachloropropane was reacted with hydrogen fluoride under certain conditions; particularly using fluorinated titanium tetrachloride as a catalyst, and operating at 80° C. to 100° C., under a pressure of 100 psig to 110 psig.

Another compound formed during this reaction is 1-chloro-3,3,3-trifluoropropene (1233zd(E)):

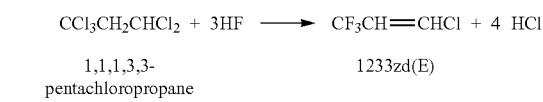

The compound 1233zd(E) is removed from the top of a distillation column connected to the reactor, and the compound of Formula I is removed from the bottom of the distillation column.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for the production of the compound of Formula I, 3-chloro-1,1,1,6,6,6-hexafluoro-2,4-hexadiene, comprising reacting 1,1,1,3,3 -pentachloropropane with hydrogen fluoride in the presence of a catalyst, in a reactor.

2. The method of claim 1, wherein the hydrogen fluoride is anhydrous HF.

3. The method of claim 1, wherein the catalyst is a liquid phase catalyst.

4. The method of claim 1, wherein the liquid phase catalyst comprises titanium tetrachloride.

5. The method of claim 4, wherein the catalyst comprises fluorinated titanium tetrachloride.

6. The method of claim 5, wherein the reaction is conducted at a temperature in the range of from 80° C. to 100° C.

7. The method of claim 5, wherein the reaction is conducted at a pressure of from 100 psig to 110 psig.

8. The method of claim 5, wherein another compound, 1-chloro-3,3,3-trifluoropropene, is formed during the reaction.

9. The method of claim 8, wherein the compound 1-chloro-3,3,3- trifluoropropeneis separated from the compound of Formula I, 3-chloro-1,1,1,6,6,6-hexafluoro-2,4-hexadiene.

10. The method of claim 9, wherein the compounds are separated by the use of a distillation column attached to the reactor.

11. The method of claim 10, wherein the compound 1-chloro-3,3,3- Trifluoropropene is removed from the top of the distillation column.

12. The method of claim 10, wherein the compound of Formula I, 3-chloro- 1,1,1,6,6,6-hexafluoro-2,4-hexadiene, is removed from the bottom of the distillation column.

* * * * *